United States Patent [19]
Carter

[11] Patent Number: 6,130,206
[45] Date of Patent: Oct. 10, 2000

[54] TREATING VIRAL INFECTIONS ASSOCIATED WITH CHRONIC FATIGUE WITH DSRNA

[75] Inventor: William A. Carter, Birchrunville, Pa.

[73] Assignee: HEM Research, Inc.

[21] Appl. No.: 08/376,457

[22] Filed: Jan. 23, 1995

Related U.S. Application Data

[63] Continuation of application No. 08/111,968, Aug. 26, 1993, abandoned, which is a continuation of application No. 07/922,668, Aug. 5, 1992, abandoned, which is a continuation of application No. 07/758,717, Sep. 9, 1991, abandoned, which is a continuation of application No. 07/613,450, Nov. 14, 1990, abandoned, which is a continuation of application No. 07/372,086, Jun. 27, 1989, abandoned, which is a continuation-in-part of application No. 07/220,765, Jul. 7, 1980, abandoned.

[51] Int. Cl.$^7$ ............................ A61K 48/00; C12N 15/85
[52] U.S. Cl. ............................ 514/44; 514/45; 514/49; 435/455
[58] Field of Search ................................................. 514/44

[56] References Cited

U.S. PATENT DOCUMENTS

| | | |
|---|---|---|
| 4,024,222 | 5/1977 | Ts'o et al. . |
| 4,795,744 | 1/1989 | Carter . |
| 4,950,652 | 8/1990 | Carter . |
| 5,063,209 | 11/1991 | Carter ........................................ 514/44 |

OTHER PUBLICATIONS

*Archives of Virology*, vol. 91, 1986, D.D. Pekovic et al, "Detection of HTLV–III/LAV Antigens in Peripheral Blood Lymphocytes . . . " pp. 11–19.

*Journal of Biological Chemistry*, vol. 260, No. 16, Aug. 5, 1985, D. Krause et al, "Independent Regulation of ppp(A2'p) . . . ", pp. 9501–9506.

Carter et al, The Lancet, 1286–1292, Jun. 6, 1987, "Clinical, Immunological, and Virological Effects of Ampligen, A Mismatched Double–Stranded RNA, in Patients with AIDS or AIDS–Related Complex".

Suhadolnik et al: in vivo 8:599–604 (1994) "Changes in the 2–5A Synthetase/RNase L Antiviral etc."

Suhadolnik et al: Clinical Infectious Diseases 1994:1 (suppl. 1): S96–104 "Upregulation of the 2–5A etc."

Suhadolnik et al: J. of Interferon and Cytokine Research 17:377–385 (1997) "Biochemical Evidence for a Novel Low Molecular Weight 1–5A–Dependent RNAse L in Chronic Fatigue Syndrome"

Krause et al. *J. Biolog. Chem.* vol. 260, No. 16, Aug. 15, 1985, pp. 9501–9506.

*Primary Examiner*—Deborah Crouch
*Attorney, Agent, or Firm*—Nixon & Vanderhye

[57] ABSTRACT

Virus infections promoting Chronic Fatigue can be diagnosed by assessing the 2'–5'A/RNase L pathway, including measurement of 2'–5'A oligonucleotide levels in the patient's circulating peripheral leucocytes, and comparing these resuls with those of healthy individuals. Double-stranded RNAs, notably mismatched dsRNAs, when administered in appropriate amounts, increase the 2'–5'A and normalize the antiviral pathway in patients with Chronic Fatigue Syndrome and improve the clinical symptoms.

2 Claims, No Drawings

TREATING VIRAL INFECTIONS ASSOCIATED WITH CHRONIC FATIGUE WITH DSRNA

This application is a continuation of Ser. No. 08/111,968 filed Aug. 26, 1993, abandoned, which is a continuation of Ser. No. 07/922,668 filed Aug. 5, 1992, abandoned, which is a continuation of 07/758,717 filed Sep. 9, 1991, abandoned, which is a continuation of 07/613,450 filed Nov. 14, 1990, abandoned, which is a continuation of 07/372,086 filed Jun. 27, 1989, abandoned, which is a continuation-in-part of Ser. No. 07/220,765 filed Jul. 7, 1980, abandoned.

BACKGROUND OF THE INVENTION

Chronic Fatigue Syndrome (CFS), a generic condition involving some 10 to 12 million in the United States alone, is a difficult to diagnose, ubiquitous disorder characterized by extreme fatigue, lymph gland enlargement and constitutional symptoms such as weight loss, loss of appetite, memory deterioration and loss of intelligence in some patients. The condition occurs especially in younger, active people and is associated with infections by both RNA and DNA-containing viruses. Some CFS patients manifest neuropsychiatric changes such as depression, loss of memory and similar derangements. Thus, chronic fatigue syndrome is sometimes difficult to distinguish from entirely neurological disorders, particularly situational depression. Various laboratory studies indicate that many different viruses replicate in individuals having Chronic Fatigue, and that these individuals become, in effect, "virus sewers". Viruses such as Epstein-Barr, cytomegalovirus, retroviruses, herpes viruses, etc., are often present in such individuals where they remain for years and the patients beocme progressively fatigued and bed-ridden.

I have determined that specific alterations in 2'-5'A molecular pathways exist in the majority of individuals having Chronic Fatigue Syndrome, which alterations have diagnostic and prognostic significance of enormous value. As an illustration, consider that many 25–30 year old women with very active small children at home often complain of "chronic fatigue", but are not necessarily virus-infected. The diagnostic procedures here described enable the clinician to ascertain which patients presenting symptoms of chronic fatigue and related symptoms including in some instances loss of weight, loss of appetite and neuropsychiatric changes, are properly classified as having Chronic Fatigue Syndrome with associated viral involvement and accurately distinguishing such patients from those presenting fatigue symptoms caused by other often external reasons and/or depression. Proper diagnosis of Chronic Fatigue Syndrome is the necessary prerequisite to effective therapy, which therapy is also herein described. These valuable diagnostic and therapeutic procedures are described below.

In addition to these diagnostic procedures, the first definitive therapy for this disorder has been developed using various double-stranded RNAs to correct the viral-associated disorders and successfully treat the patient's condition.

In previous studies, the diagnostic utility of individual components of the 2'-5' oligoadenylate/RNase L pathway has been reported especially as it relates to viral disorders in general and retrovirus infections in particular without particular reference to chronic fatigue symptoms. Specifically, it has now been determined that in Chronic Fatigue Syndrome, among other things, an abnormally low 2'-5'A synthetase enzyme and an aberrantly activated RNase L enzyme, both integral parts of the cell's natural antiviral pathway, exist and correlate with the morbid fatigue condition. These two measurements thus can act as indicators or "markers" for Chronic Fatigue Syndrome and thus can be used to definitively diagnose, and follow treatment of, the syndrome in a wholly new and clinically reliable manner. Further, the diagnosis is conveniently performed from a patient's peripheral blood sample without the need for surgery or other invasive diagnostic tests.

DESCRIPTION OF THE INVENTION

This invention includes procedures for identifying Chronic Fatigue Syndrome, as evidenced by a viral-associated aberration of RNase L enzyme coupled with low level of 2'-5'A synthetase enzyme in the patient's peripheral blood lymphocytes, diagnostic procedures using this information to determine the presence of Chronic Fatigue Syndrome, therapeutic procedures for restoring the patient's 2'-5'A molecular pathway aberrations such as by administering exogenous dsRNAs and improving the patient's clinical condition, therapeutic procedures for monitoring a Chronic Fatigue Syndrome patient's condition and gauging the degree of dsRNA replacement required on an individual basis, and therapeutic compositions for treating Chronic Fatigue Syndrome.

Diagnostic Procedures

The in vivo concentration of 2'-5'A synthetase enzyme, 2'-5'A molecules, and activated RNase L in normal individuals and subjects with Chronic Fatigue Syndrome was assessed from patient samples (Ficoll-Hypaque-purified peripheral blood lymphocytes). The 2–'5'A content was determined by 2'-5'A core-cellulose assays (affinity chromatography) with poly U-$\{^{32}P\}$-pCp. In this assay, the ability of 2'-5'A-activated RNase L to hydrolyze poly(U) is used to determine the concentration of functional 2'-5'A.

Reference values were established by testing 25 normal subjects with no recent history of viral infections as evidenced by lack of virus-culturability, fever, absence of constitutional symptoms, rashes, etc. Concentrations of the test subject's lymphocyte 2'-5'A levels were determined using calibration curves obtained with authentic 2'-5'A molecules. Normal individual reference values, expressed as nanamoles of 2'-5'A per gram of lymphocyte protein, are generally within the range of 0.2 to 1.0. Normal calibration curves were also established for the 2'—5'A synthetase enzyme and RNase L enzyme.

Using these assay methods, ten patients exhibiting the usual symptoms of Chronic Fatigue Syndrome were tested and the representative results are summarized below. 2'-5'A oligonucleotide levels are typically increased about 2–15 fold while 2'-5'A synthetase enzyme is proportionally decreased and a novel RNase L enzymic aberrancy arises.

TABLE 1

Pre-Therapy Aberrations in
2'–5' A/RNase L Pathway in Patients Experiencing
Chronic Fatigue Secondary to Viral Infection

| Subject Nunber | n moles 2'–5' A per gram lymphocyte protein |
|---|---|
| A | 1.4, 2.4 |
| B | 2.0 |
| C | 10.1 |
| D | 5.2 |
| E | 11.3 |
| F | 7.6 |
| G | 8.3 |
| H | 4.7 |
| I | 3.8 |
| J | 5.9 |

Also, all 10 subjects prior to dsRNA therapy showed depression of intracellular 2'–5'A synthetase enzyme to levels approximately 5 to 50 fold below that of healthy, uninfected subjects. Patients with Chronic Fatigue Syndrome have generally an associated defect (or aberration) in the terminal mediator of the antiviral defense pathway termed RNase L. Thus, the entire antiviral defense pathway demonstrates both defects (altered levels of mediators) or aberrancies (new activities of enzyme components). Definitive treatment of such individuals with Chronic Fatigue Syndrome is provided by supplying exogenous dsRNAs, as required, until the intracellular level of 2'–5'A oligonucleotides and 2'–5'A synthetase reaches normal, the RNase L aberration is corrected, and/or the patient's clinical symptomology abates. Often these molecular improvements occur apparently contemporaneously with dramatic clinical improvements, as noted by comparing Table 2 (an enzymatic pathway studied over time in patient A) with clinical charts of patient A (Tables 3 and 4). More than 90% of the other patients studied to date had similar dramatic enzymatic improvements associated with clinical recovery.

TABLE 2

COMPONENTS OF THE 2-5A SYNTHETASE/RNase ANTIVIRAL SYSTEM IN PBMC FROM CHRONIC FATIGUE SYNDROME (CFS) PATIENTS

| PBMC Source | Weeks on mismatched dsRNA | 2-5A Synthetase Activity In Vitro[a] | Intracellular Concentration of 2-5A[b] | Activated RNase L[c] |
|---|---|---|---|---|
| CFS Patient #A | 0 | 2.4 | 1.4 | ++++ |
| | 0 | 1.8 | 2.4 | ++++ |
| | 2 | 1.4 | 0.5 | +++ |
| | 4 | 2.1 | 0.7 | + |
| | 8 | 1.4 | 0.6 | + |
| Healthy | | 5 | 0.7 | + |

[a]nmoles ATP incorporated into 2-5A per mg protein
[b]nmoles per gram protein
[c]+ = normal level; ++++ = "hyperactive" RNase L level as measured in rRNA cleavage assay.

TABLE 3

Cumulative Neuropsychological Test Scores

| | | | Ampligen Started | |
|---|---|---|---|---|
| Test | 8/26/87 | 5/26/88 | 6/30/88 ↓ | 9/1/88 |
| Wais - R | | | | |
| Information | 12 | 13 | 11 | 15 |
| Digit Span | 11 | 8 | 8 | 10 |
| Vocabulary | 12 | 12 | 12 | 16 |
| Arithmetic | 9 | 8 | 5 | 11 |
| Similarities | 15 | 13 | 9 | 12 |
| Block Design | 8 | 6 | 5 | 9 |
| Digit Symbol | 8 | 2 | 3 | 8 |
| Full Scale IQ | 110 | 98 | 88 | 112 |
| Halstead - Reitan | | Impairment Levels | | |
| Hand Tapping | Severe | Severe | Severe | Normal |
| Trailmaking A | Mild | Severe | Severe | Normal |
| Trailmaking B | Mild | Mild | Moderate | Normal |

TABLE 4

Exercise Tolerance Test

| Date | Stage | Duration |
|---|---|---|
| 7/23/88 | I | 1 min, 30 sec |
| 8/9/88 | Ampligen Therapy Started | |
| 9/6/88 | I | 3 min |
| 10/20/88 | II | 3 min |
| | III | 5 min |
| 12/6/88 | I | 3 min |
| | II | 6 min, 10 sec |
| 4/4/89 | II | 3 min |
| | III | 6 min |

The patient's resistance to Chronic Fatigue Syndrome and opportunistic viruses can be maintained by continuing to measure the patient's intracellular 2'–5'A oligonucleotide levels, 2'–5'A synthetase, and degree of aberrancy in RNase L enzyme, and by supplying exogenous dsRNA, as required, to maintain normalcy, or near normalcy, of these molecular functions.

The natural (intracellular) dsRNAs also play a role in host defense when an individual is challenged with viral agent(s) such as in Chronic Fatigue Syndrome. Specific reduction in bioactive dsRNA, or enzymes which depend directly or indirectly on dsRNA, notably 2'–5'A synthetase and aberrant RNase L, coupled with abnormally low levels of 2'–5'A in peripheral blood lymphocytes, within specific cells contributes to viral disease chronicity, whatever the specific viral agent. dsRNA, notably mismatched dsRNAs (such as AMPLIGEN®, HEM Research, Inc., Rockville, Md., USA), reverses disease symptomology by re-regulating the deranged molecular pathway.

By "mismatched dsRNA" are meant those in which hydrogen bonding (base stacking) between the counterpart strands is relatively intact, i.e., is interrupted infrequently. The term "mismatched dsRNA" should be understood accordingly. The dsRNA may be a complex of a polyinosinate and a polycytidylate containing a proportion of uracil bases or guanidine bases, e.g., from 1 in 5 to 1 in 30 such bases (poly I·poly($C_{4-29}$x>U or G)).

The dsRNA may be of the general formula $rI_n·r(C_{11-14}, U)_n$ or $rI_n·r(C_{12},U)_n$. Other suitable examples of dsRNA are discussed below, and specific double-stranded oligonucleotides can also be deployed in certain instances.

The mismatched dsRNAs preferred for use in the present invention are based on copolynucleotides selected from poly $(C_n,U)$ and poly $(C_n,G)$ in which n is an integer having a value of from 4 to 29 are mismatched analogs of complexes of polyriboinosinic and polyribocytidilic acids, formed by modifying $rI_n \cdot rC_n$ to incorporate unpaired bases (uracil or guanidine) along the polyribocytidylate ($rC_n$) strand. Alternatively, the dsRNA may be derived from poly(I)·poly (C) dsRNA by modifying the ribosyl backbone of polyriboinosinic acid ($rI_n$), e.g., by including 2'-O-methyl ribosyl residues. The mismatched complexes may be complexed with an RNA-stabilizing polymer such as lysine and cellulose. These mismatched analogs of $rI_n \cdot rC_n$, preferred ones of which are of the general formula $rI_n \cdot (C_{11-14},U)_n$ or $rI_n 1 \cdot r (C_{29}, G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:

poly(I)·poly($C_4$,U)

poly(I)·poly($C_7$,U)

poly(I)·poly($C_{13}$,U)

poly(I)·poly($C_{22}$,U)

poly(I)·poly($C_{20}$,G)

poly(I)·poly($C_{29}$,G)

and poly(I)·poly$C_{p23}$G>p

Oligonucleotide dsRNA molecules may also be used in which the molecular "ends" are hinged to prevent slippage of the base pairs, thereby conferring a specific bioactivity in a variety of solvent or aqueous environments which exist in human biological fluids.

2'–5'A concentration and molecular size may be quantitated by high pressure liquid chromatography (HPLC). Ribosomal RNA cleavage assays may be used to assess biological functionality (activity) of the 2'–5'A-synthesized by the patient in vivo and to determine the level of activated RNase L in patient samples. Peripheral mononuclear blood cells are the preferred cells for analysis although other cells may be analyzed if the chronic virus infection s is sequestered in other body organs.

Patients having Chronic Fatigue Syndrome are treated typically with intravenous infusions of 200 to 600 mg of $rI \cdot r(C_{11-14},U)$ twice or three times weekly or until 2'–5'A levels increase in association with clinical improvement and correction of synthetase levels and RNase L aberrancy occurs. The amount of dsRNA administered and the frequency of administration will be guided by these laboratory parameters measured in conjunction with the patient's clinical improvement. Amounts of dsRNA administered will provide a transient level of from 0.01 to 1,000 micrograms of dsRNA per milliliter of the patient's systemic blood circulation immediately following administration measured at a point distal from the point of infusion. Bioactive fragments of dsRNA, breakdown products of the infused macromolecular dsRNA, serve to sustain the 2–5A enzymatic pathway improvements, thus enhancing the clinical recovery process.

What is claimed is:

1. A method of treating the symptoms of chronic fatigue syndrome in a person suffering therefrom, comprising administering into the blood system of a person in need of same an effective amount of poly I·poly($C_{12}$,U).

2. The method of claim 1 in which the poly I·poly($C_{12}$,U) administered results in a level of from 1 to 1,000 micrograms of the polyI·poly($C_{12}$,U) per milliliter of the patient's systemic blood circulation.

* * * * *